United States Patent [19]

Hudnutt et al.

[11] Patent Number: 4,625,405
[45] Date of Patent: Dec. 2, 1986

[54] CAST CUTTER

[75] Inventors: H. Dean Hudnutt, Benton Harbor, Mich.; Edsell M. Eady, Bradfordwoods; Mark V. Cromie, Pittsburgh, both of Pa.

[73] Assignee: Deeco, Inc., Pittsburgh, Pa.

[21] Appl. No.: 626,650

[22] Filed: Jul. 2, 1984

[51] Int. Cl.⁴ ............................................. B23D 47/02
[52] U.S. Cl. ........................................ 30/370; 30/390; 128/317
[58] Field of Search ...................... 30/124, 166, 166 D, 30/350, 351, 388, 370, 390; 128/305, 317; 83/835

[56] References Cited

U.S. PATENT DOCUMENTS 1,876,337  9/1932  Mead ............................... 30/124 X
2,330,952 10/1943  Christen et al. ...................... 30/124
2,522,006  9/1950  Wilcox ................................. 30/124

FOREIGN PATENT DOCUMENTS 478354 6/1929 Fed. Rep. of Germany ...... 128/317
322599 11/1934 Italy .................................. 128/317

Primary Examiner—E. R. Kazenske
Assistant Examiner—Willmon Fridie, Jr.
Attorney, Agent, or Firm—Pearne, Gordon, Sessions, McCoy, Granger & Tilberry

[57] ABSTRACT

A cast cutter having a pair of juxtaposed, sawedged blades which oscillate relative to each other on a common pivot point to provide a scissorslike cutting action resulting in a relatively wide kerf in the cast being out. A patient protective blade guard, slidable between the underside of the cast and the patient's skin, includes an aperture into which portions of the blades partially extend wherein a nip area is provided at an interface location of the blades and the guard to facilitate cutting of an inner woven cloth lining of the cast to the scissor teeth. The oscillatory motion of the blades relative to each other minimizes clogging thereof by dust particles generated during a cutting operation. The blades are slightly spaced from each other to preclude friction generated heat buildup that could result from the moving blades rubbing together.

10 Claims, 8 Drawing Figures

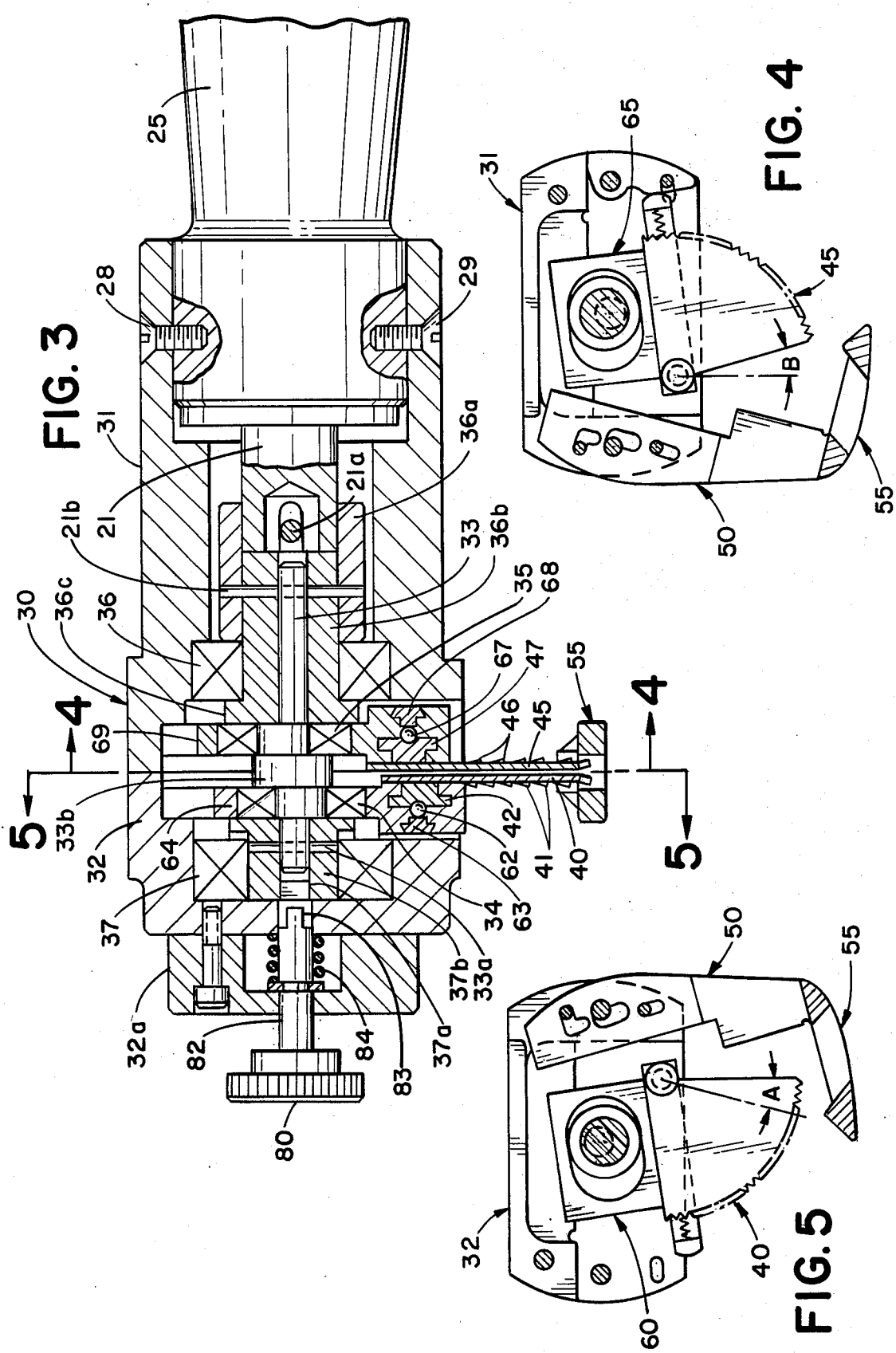

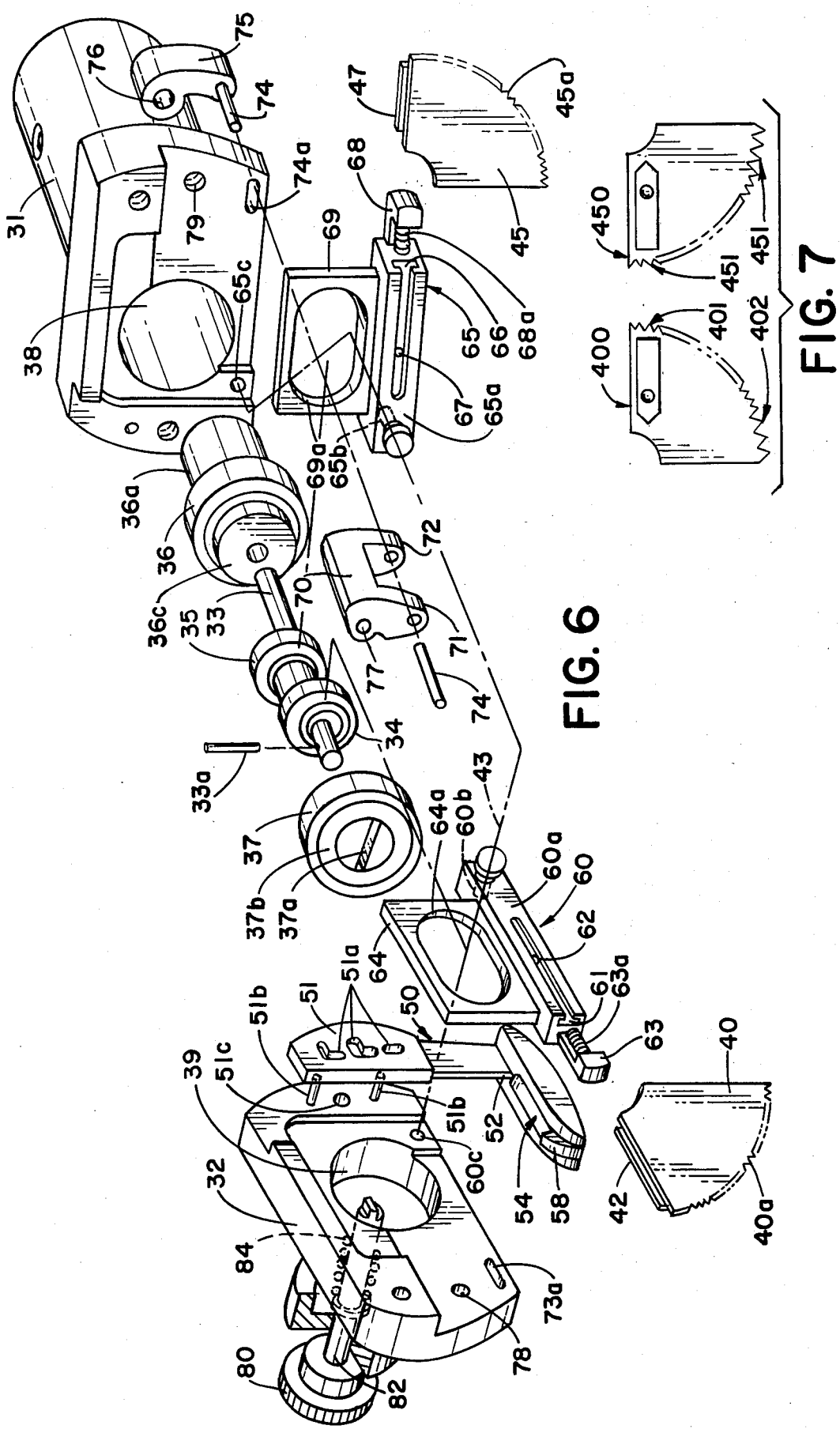

CAST CUTTER

BACKGROUND OF THE INVENTION

The present invention relates in general to an electrically powered cutting apparatus, and more particularly to a cast cutter for shearing completely through a multilayer surgical or orthopedic cast without injury to the underlying body portion of the patient.

Numerous cast cutters have been proposed for effecting the safe and non-traumatic removal of a cast from a patient. For example, see U.S. Pat. Nos. 2,232,733; 2,492,156; 3,103,069; 3,481,036; 3,533,161; 3,973,324 and 4,421,111. To the best of the inventors' knowledge, none of these patented cast cutters or other prior art cast cutters of which the inventors are aware, meet the requirements of an ideal cast cutter as specified below.

An ideal cast cutter must be able to easily cut through a multilayer plaster or fiberglass cast, while insuring that the underlying body portion of the patient, which is often swollen, is not cut or further traumatized during cast removal.

A typical cast often includes a woven cloth wrapping or sleeve that is initially applied to the patient's skin. A cottonlike fibrous layer of padding material is usually applied over the woven cloth sleeve. A wet plaster or uncured fiberglass wrapping is then applied over the fibrous layer, the plaster or fiberglass wrapping eventually hardening to provide a rigid, three layer cast for immobilizing the body portion that it surrounds.

An ideal cast cutter must be able to simultaneously cut completely through the inner woven cloth sleeve, the intermediate fibrous layer of padding material, and the outer rigid plaster or fiberglass layer of the cast. Further, such multilayer cutting must be accomplished while protecting the underlying body portion of the patient. Also, the cast cutter should be relatively quiet in operation, and should not appear threatening to the patient whose cast is being removed. In addition, the cast cutter should be designed for easy manipulation by the user. Finally, the ideal cast cutter should be highly reliable in its operation, reasonable in cost, and relatively simple in structure.

SUMMARY OF THE INVENTION

In accordance with the present invention, an apparatus is provided for safely and efficiently cutting a surgical or orthopedic cast overlying a human or animal body portion.

The apparatus includes a motor means mounted to a housing. A pair of blade members, each having an arcuate, sawtoothed, edge portion, the edge portions being in juxtaposed relation, are pivotally mounted relative to the housing for concurrent movement on a common pivot axis.

A transmission means is located within the housing and is connected between the motor means and the blades. The transmission means has an input connected to the motor and an output connected to the blades. The transmission means, in response to energization of the motor means, simultaneously drives the blades for oscillatory movement relative to each other, the juxtaposed edge portions being at least in part simultaneously engageable with the cast to cut the cast and provide a relatively wide single kerf therein. A footlike blade guard is supported in fixed relationship to the blades. The guard is positionable between blade portions engageable with the cast and the underlying body portion of the patient so as to shield the patient's body portion from contact with the moving blades as the cast is cut.

In a preferred form, the blade guard has an upper surface engageable with the underside of the cast and a lower surface engageable with the body portion of the patient. The sawtoothed edge portions of the blades extend to the upper surface of the blade guard to provide a nip area for receiving the underside of the cast engageable with the blade guard upper surface. The sawtoothed, arcuate, edge portions of the blades move in parallel planes generally perpendicular to the upper surface of the footlike blade guard.

It has been found that the use of arcuate-edged oscillating blades, cooperating with a footlike blade guard to provide a nip area for receiving the inner layer of the cast, e.g. a woven cloth inner layer, provides for very efficient cutting of a cast. A relatively wide kerf, resulting from the scissorslike shearing and abrading action of the oscillating blades, allows the user to easily separate the cast along the kerf line thereby facilitating cast removal. Further, the cutting action provided in accordance with the invention easily shears through a multilayer cast including an inner woven cloth layer, an intermediate cottonlike fibrous layer of padding material, and an outer plaster or fiberglass layer. Also, the presence of the protective footlike blade guard reassures the patient that contact of the underlying body portion of the patient with the moving blades is effectively precluded thus lowering the anxiety level that the patient might otherwise experience if presented with an open blade type cast cutter which provides no protection from accidental cutting of the patient's skin during cast removal. The preferred embodiment of the invention also provides for easily removable blades, of a novel design, that can be replaced when worn. Also, the configuration of the blades and their movement relative to each other directs and channels dust particles generated during cutting to areas easily accessible for pickup by a conventional vacuum type dust collector.

BRIEF DESCRIPTION OF THE DRAWINGS

A fuller understanding of the invention may be had by referring to the following description and claims taken in conjunction with the accompanying drawings, wherein:

FIG. 3 is a sectional view of a transmission and blade end of the cast cutter;

FIG. 4 is a cross section view taken along line 4—4 of FIG. 3;

FIG. 5 is a cross section view taken along line 5—5 of FIG. 3;

FIG. 6 is an exploded view of the transmission and blade end of the cast cutter; and FIG. 7 is a perspective view of another embodiment of a novel blade member for use with the cast cutter of the present invention.

DETAILED DESCRIPTION OF THE PREFERRED EMBODIMENT

Figure 1:
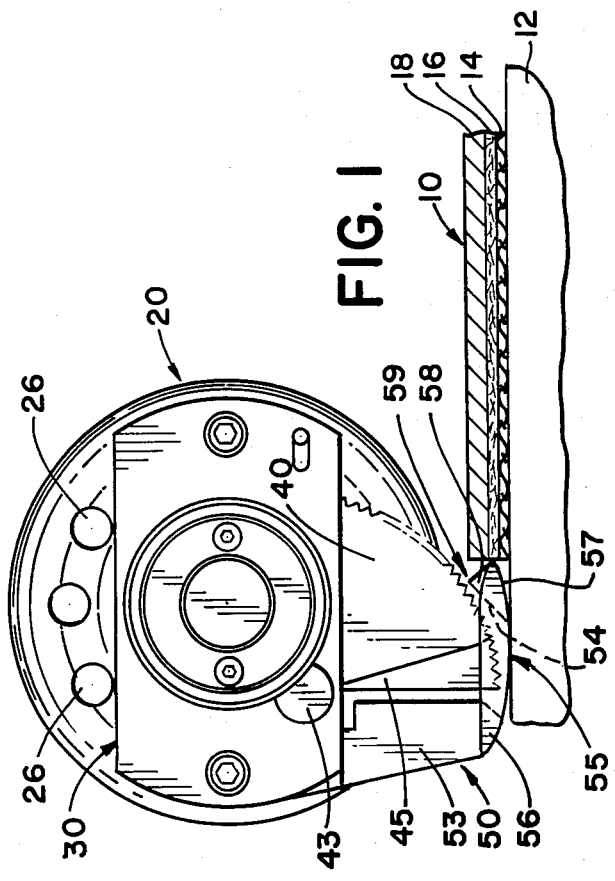
FIG. 1 is a cross section view of a multilayer cast about to be cut by a cast cutter (end view) in accordance with the present invention.
Figure 1A:
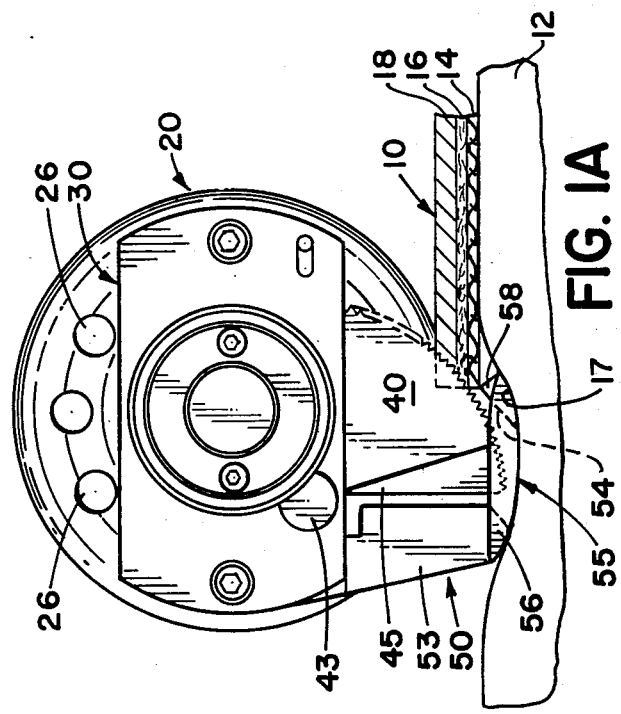
FIG. 1A is a cross section view of the cast as it is being cut by the cast cutter.
Figure 2:
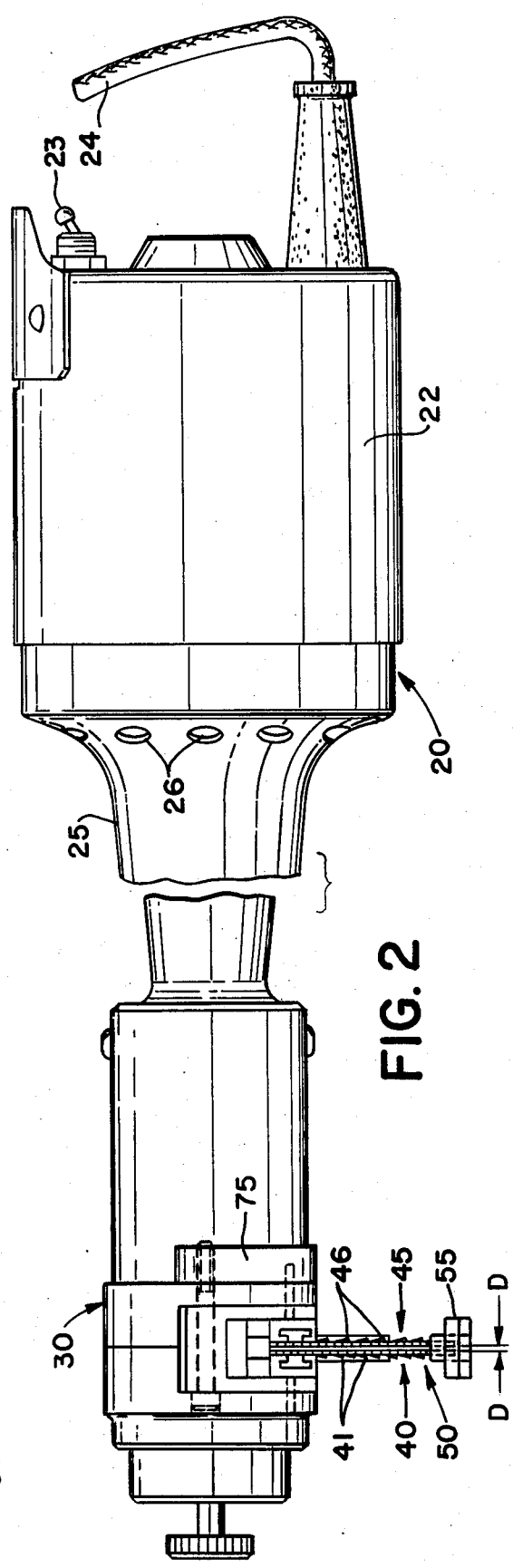
FIG. 2 is an elevation view of the cast cutter illustrated in FIG. 1.

With reference to FIGS. 1, 1A and 2, there is illustrated an apparatus for cutting a surgical or orthopedic cast 10 which overlies a human or animal body portion 12. The cast 10 is typically formed of multiple layers of material. For example, an inner sleeve layer of woven meshlike cloth 14 is applied directly to the body portion 12 of the patient. An intermediate cottonlike fibrous layer of padding material 16 is then applied on top of the meshlike cloth 14 to act as a cushioning buffer between the underlying body portion 12 of the patient and an outer layer 18 of rigid plaster or fiberglass for immobilizing the body portion that it surrounds.

In accordance with the present invention, a novel cast cutter is provided for simultaneously cutting through the multiple layers 14, 16, 18 of the cast 10 to provide a relatively wide groove or kerf allowing the user to easily separate the cast along the kerf to permit its removal from around the body portion 12 of the patient.

As illustrated most clearly in FIG. 2, the cast cutter includes at its rearward end (or right end as viewed in FIG. 2) a motor means 20 preferably in the form of a common electrical induction motor operating at standard 60 hertz 120 volt AC power. It is to be noted that other motor means, e.g. a compressed air driven turbine motor, or hydraulically driven motor could be utilized. An electric motor successfully used in practicing the present invention is of a one tenth horse power size providing a motor shaft revolution speed of approximately 20,000 revolutions per minute. The illustrated motor means 20 includes an elongated rotor and commutator containing cylindrical casing portion 22 and a forward tapered casing portion 25 extending toward the front of the cast cutter (leftward end as viewed in FIG. 2). The rearward end (or right end as viewed in FIG. 2) of the casing portion 22 includes a conventional on-off toggle switch 23, and a power cord 24 for connecting the motor means 20 to a source of electrical power. The switch 23 could take other forms than that illustrated. For example, a squeeze-type switch in the hand grip region, i.e. tapered casing portion 25, could be utilized. The forward tapered casing portion 25, grippable by the user, houses an extended distal end of a rotor driven motor shaft to be illustrated subsequently in greater detail. The motor means 20 is air cooled in conventional fashion by air being exhausted from a plurality of air outlets 26, the air being drawn into the casing portion 22 via air inlets (not shown) located at the rear end of the casing portion 22.

The distal end (or leftward end as viewed in FIG. 2) of the forward tapered casing portion 25 is mounted to a housing 30 which contains a transmission means for driving a pair of generally identical, but complementary blade members 40, 45 in oscillatory fashion relative to each other. The term "generally" identical as used above means that the blades are identical but for their being mirror images of each other so that one blade is considered a left handed blade, the other blade being considered a right handed blade, i.e. the blades complement each other. As shown most clearly in FIG. 1, the blade members 40, 45 extend downwardly from the housing 30 to interface with a footlike blade guard 50 which is supported in fixed relation to the housing 30 in a manner to be subsequently illustrated in greater detail. The blade guard 50 includes a vertical leg portion 53 which extends downwardly from the housing 30 for supporting a perpendicular foot portion 55 having a heel end 56 and a toe end 57. A small toothlike projection 58 extends upwardly from the toe end 57 of the foot portion 55 so as to be spaced slightly from the blade members 40, 45 as illustrated. The space between the tip of the projection 58 and the blade members 40, 45 constitutes a nip area having a width of approximately 0.005 of an inch. It can further be seen that the foot portion 55 of the blade guard 50 includes an aperture 54 which extends from the upper surface of the foot portion to its lower surface. The aperture 54 receives the lower end portions of the blade members 40, 45 which oscillate relative to each other about a common pivot axis 43 provided by the housing 30, the end portion being contained within the aperture between the upper and lower surfaces of the foot portion 55.

With particular reference to FIG. 2, it can be seen that the juxtaposed complementary blade members 40, 45 lie in parallel planes that are generally perpendicular to the upper surface of the foot portion 55 of the blade guard 50. It can also be seen that the platelike blade members 40, 45 respectively include arcuate sawtoothed edge portions 40a, 45a (see FIG. 6) these edge portions having outwardly pitched sawteeth projections, 41, 46, as viewed in FIG. 2, extending from their outboard sides (i.e. the sawteeth projections of one arcuate edge portion extend outwardly away from the other edge portion), but not from their inboard opposed planar sides, so as to preclude interference between the blades along their inboard faces as they oscillate relative to each other. The outwardly pitched sawteeth projections also advantageously provide a kerf having a width exceeding that of the combined widths of the non-toothed portions of the two blades, a wide kerf facilitating removal of the cast. With reference to FIG. 2, it can be seen that the inboard planar faces of the blade members 40, 45 are slightly spaced from each other to preclude their rubbing together so as to avoid the generation of undesired frictional heat. It is to be noted that this spacing distance D—D is exagerated in FIG. 2 for illustration purposes and in fact is only on the order of 0.002 to 0.005 of an inch.

With reference to FIGS. 1 and 1A, the operation of the illustrated cast cutter in cutting through the multilayer cast 10 will now be discussed. The operator will normally grip the cast cutter by the tapered casing portion 25 which is located approximately at the center of gravity of the cast cutter so as to facilitate balancing of the cutter in the hand of the user. With the blades 40, 45 oscillating at a high rate of speed relative to each other through a relatively small angular sector as will be illustrated subsequently, the toe end 57 of the foot portion 55 is slipped under an end of the cast 10 (see FIG. 1A) wherein the inner sleeve layer of projection 58 and will be received in the nip area 59 where it will be sheared by the scissorslike oscillating action of the blade members 40, 45. In a similar fashion, the fibrous layer of padding material 16 and the rigid outer plaster or fiberglass layer 18 will be sheared and abraded by the arcuate sawtoothed edge portion of the blades 40, 45. It has been found that by providing a relatively narrow nip area 59 that the inner woven cloth layer 14 of the cast can be easily cut simultaneously with the cutting of the intermediate layer 16 and the abrading of the outer layer 18 of plaster or fiberglass. It has also been found that dust particles generated during the cutting process are exhausted, at least to a degree, downwardly into the trailing kerf area through the aperture 54 provided in the foot portion 55 so as to preclude clogging of the blades 40, 45. That portion of the dust particles not exhausted through aperture 54 can be picked up by a conventional vacuum means (not shown) associated with the illustrated cast cutter. This shearing, cutting, and abrading action of the relatively fine toothed, high speed, dual oscillating blades 40, 45 provides a wide kerf or groove in the cast 10 thus facilitating removal of the cast once a complete longitudinal cut or more than one longitudinal cut has been made along the length of the cast. During the cutting operation, the foot portion 55 of the blade guard 50 is located between the cast being cut and the underlying body portion of the patient so as to preclude accidental cutting of the patient by the saw blades.

With reference to FIG. 3, the housing 30 for the transmission means can be seen to be comprised of a first cylindrical housing half 31 and a second cylindrical housing half 32, the halves 31, 32 being fastened together by a plurality of conventional bolts (not shown). As viewed in FIG. 3, the rightward end of the first housing half 31 includes a central bore for receiving the distal end of the tapered casing portion 25 of the motor means. Mounting screws 28, 29 extend through opposed transverse apertures in the end of the housing half 31 and extend into the end of the casing portion 25 as illustrated so as to rigidly fix the housing half 31 onto the end of the casing portion 25, the casing portion 25 surrounding the motor output shaft 21 having a distal end that extends into the interior of the housing half 31.

An elongated transmission drive shaft 33 (also shown in FIG. 6), constituting a transmission input means, is rotatably mounted within the housing halves 31, 32 of the transmission housing 30 by means of a first main bearing 36 carried in the housing half 31 and a second main bearing 37 carried in the housing half 32. The bearings 36, 37 are conventional and each includes an outer race portion fixed in position within the housing 30 and an inner race portion rotatable relative to the outer race portion. An annular collar member 36a fits over the end of the motor shaft 21 and is fixed thereto by means of a locking pin 21a that extends diametrically through both the shaft 21 and the collar 36a. The other end of the collar member 36a abuts one side of the inner race portion of the bearing 36 and also receives a reduced diameter end of an annular drive shaft support 36b which has a central bore for receiving one end of the transmission drive shaft 33 which is rotationally fixed to the collar member 36a by a second locking pin 21b that extends diametrically through the collar 36a, the support 36b, and the shaft 33 as illustrated in FIG. 3. It can be seen that the collar 36a and the support 36b, having a flanged edge 36c sandwich the inner race portion of the bearing 36 between them, wherein the elements 33, 36a, 36b, and 21 will rotate as a unit within the housing 30.

In a similar fashion, the other end of the transmission drive shaft 33 is received into a central bore in a generally cylindrical drive shaft support 37b which engages the inner race portion of the second main bearing 37. A third locking pin 33a diametrically extends through the support 37b and the end of the shaft 33 as illustrated. Thus, it can be seen that the shaft 33 is rotatably supported within the housing 30 by means of the bearings 36, 37 and associated elements as discussed above.

With reference to FIGS. 3 and 6, an intermediate portion of the shaft 33 provides a first eccentrically mounted circular cam member 34 and a second eccentrically mounted circular cam member 35 separated by a spacer member 33b as illustrated. The bearinglike eccentric members 34, 35 rotate with the shaft 33 and cause oscillatory motion of the blade members 40, 45 relative to each other, the eccentric members being 180 rotational degrees out of phase with each other, i.e. the high spots or lobes of the circular eccentric members are located opposite to each other relative to the axis of rotation of the shaft 33.

With particular reference to FIG. 6, such oscillatory motion is provided by a first blade holder 60 and a similar, but complementary, second blade holder 65, the blade holders 60, 65 constituting transmission output means. The blade holders 60, 65 are mounted to the respective housing halves 32, 31 for pivotal movement on the pivot axis 43 (also see FIG. 1) by means of pivot pins 60b, 65b received in pin receiving, bushinglike apertures 60c, 65c provided in the housing halves 32, 31. A base portion 60a of the first blade holder 60 includes a first blade mounting groove 61 having a T-shaped cross section as illustrated. The groove 61 is sized to receive an associated first blade mounting slide 42, also having a T-shaped cross section, fixed to the blade 40 along its upper edge as illustrated. The mounting slide 42 is received into the groove 61 and held in position therein by a first movable detent ball 62 that fits into a recess in the outer surface of the slide 42. With particular reference to FIG. 3, a movable detent release slide 63 acts as a camming surface that normally holds the ball 62 in its locked position in the recess of the mounting slide 42. When the detent release slide 63 is pressed further into an associated slide receiving T-shaped groove in the base portion 60a of the blade holder 60, against the force of a biasing spring 63a, the ball 62 is allowed to move out of the recess in the slide 42 and into a complementary recess (not shown) provided in that face of slide 63 engageable with detent ball 62 wherein the blade 40 can be easily slid out of the blade holder 60.

In a similar fashion, a second blade holder 65 (see FIG. 6) having a base portion 65a includes a second blade mounting groove 66 for receiving a second blade mounting slide 47 fixed to the blade 45 as illustrated. A second detent release slide 68 can be moved inwardly against the force of a second biasing spring 68a to allow removal of the blade 45 from the slide mounting groove 66 where it is normally held in position by a second detent ball 67 received in a recess in the slide 47 as illustrated most clearly in FIG. 3.

It can thus be seen, that the blades 40, 45 are received in their respective blade holders 60, 65 and locked in position therein by means of the respective detent balls 62, 67. When the detent release slides 63, 68 are actuated, the detent balls 62, 67 are movable out of the respective recesses in the slides 42, 47 to allow easy extraction and insertion of the blades from the blade holders 60, 65. Simultaneous actuation of the detent release slides 63, 68 is provided by a detent release member 70 having a first leg 71 engageable with the exposed end of the detent release slide 63 and a second leg 72 engageable with the exposed end of the second detent release slide 68. Associated with the detent release member 70 is a detent release trigger 75 which can be manually actuated by the user since it is located outside of the housing 30 (see FIG. 2). With further reference to FIG. 6, the members 70, 75 pivot together about a common axis provided by a bolt member (not shown) that extends through bore 78 of the housing half 32, bore 77 of the detent release member 70, bore 79 of the housing half 31 and bore 76 of the detent release trigger 75. A pin 74 (shown in two parts) connects the release trigger 75 and the detent release member 70 together for concurrent movement. When, for example, the thumb of the user is pressed inwardly, against trigger 75, towards the housing half 31 to cause rotation of the detent release trigger 75 against the force of the biasing spring 63a, 68a, the detent balls 62, 67 are allowed to move out of their locking position in the recesses (see FIG. 3) in the slides 42, 47, wherein extraction or insertion of the blade members 40, 45 can be effected. It can be seen that a relatively simple mechanism has been provided for facilitating the insertion and extraction of the blade members 40, 45.

With particular reference to FIGS. 4 and 5, the foot portion 55 of the footlike blade guard 50 can, when the housing halves are slightly separated from each other by loosening the bolts joining such housing halves together, be pulled downwardly to a slight degree and then tilted away from the bottom portions of the blades 40, 45 to permit and facilitate their extraction and insertion since the blades normally project into the aperture 54 (see FIGS. 1 and 6) in the foot portion 55. Downward movement and pivoting of the blade guard foot portion 55 away from the bottom portion of the blades 40, 45 is permitted by suitably configured slots 51a, located at the upper end 51 of the blade guard 50, that receive pins 51b, and a bolt (not shown) extending through a bore 51c of the second housing half 32 as illustrated most clearly in FIG. 6. When the blades 40, 45 are inserted and locked in position within the blade holders 60, 65 the footlike blade guard 50 is manually moved to its normal position as illustrated in FIGS. 1 through 3, and then the housing halves 31, 32 are securely fastened together to clamp the upper end 51 of the leg portion 53 of the blade guard 50, the lower end 52 of the leg portion 53 having the heel end 56 of the foot portion 55 connected thereto.

It is to be noted that other unlocking or release means could be provided to permit downward and outward movement of the foot portion away from the blades 40, 45 to facilitate blade removal and insertion.

With reference to FIG. 6, the first and second circular eccentric cam members 34, 35 illustrated in the form of bearings or bushings, are fixed in position by suitable means on the intermediate portion of the drive shaft 33. The first blade holder 60 has, extending upwardly from its base portion 60a, a cam follower member 64 having an aperture therein defined by a continuous wall portion 64a. The aperture defined by the wall portion 64a receives the first eccentric cam member 34, the wall 64a acting as a cam follower riding on the outer circular surface of eccentrically mounted cam member 34 wherein the blade holder 60 pivots or reciprocates through a small angular sector (such as angle A, see FIG. 5). In a similar fashion, the second blade holder 65, having a base portion 65a is provided with an upwardly extending cam follower member 69 having an aperture therein defined by a wall 69a which acts as a cam follower engageable with the outer circular surface of the second eccentrically mounted cam member 35. As the eccentrically mounted member 35 rotates with the shaft 33, the blade holder 65 will pivot and reciprocate about axis 43 to provide movement of the blade 45 through a small angular sector (such as B illustrated in FIG. 4).

With reference to FIGS. 3 through 6 it can be appreciated that, upon rotation of the transmission drive shaft 33 by means of the motor shaft 21 the blade members 40, 45 will oscillate relative to each other through relatively small angular sectors of motion as illustrated by angle sectors A and B of FIGS. 4 and 5.

To facilitate insertion and removal of the blades 40, 45 into and out of the blade holders 60, 65 manual rotation of the shaft 33 is provided by an axially movable, rotatable shaft 82 mounted on the front end of the housing 30 by means of a subhousing 32a (see FIG. 3) the shaft 82 having an actuator knob 83 at its outer end and a screw driver type blade projection 83 at its inner end, the projection 83 being insertable into a slot 37a at the end of the bearing support 37b. The blade projection 83 is normally held out of engagement with the slot 37a by means of a biasing spring 84. When the user wants to manually rotate the shaft 33, actuator knob 80 is pressed inwardly and then rotated until projection 83 drops into slot 37a wherein shaft 33 can be rotated without energization of the associated drive motor. When actuator knob 80 is released, the biasing spring 84 will withdraw the edge projection 83 out of the slot 37a to permit high speed rotation of the shaft 33 by the motor without corresponding rotation of the shaft 82.

From all of the above, it can be appreciated that blade removal and replacement can easily be accomplished by the user without specialized tools and the like.

FIG. 7 illustrates another embodiment of platelike blade members 40, 45. With reference to FIG. 6, it can be seen that the edge portions 40a, 45a of the blade members 40, 45 are provided with relatively fine sawteeth projections having equal density or pitch. With reference to FIG. 7, it can be seen that the lower portions or sections of alternative blade members 400, 450 are provided with fewer but larger teeth members 402, 452 having a relatively deep root. On the upper portions or sections of the blade members 400, 450, the teeth 401, 451 are smaller and of a greater density or pitch, each have a relatively shallow root. Such a blade structure will advantageously provide for a scissorslike shearing action of the inner woven cloth layer of the cast by the larger blade teeth, while the other higher pitch teeth would provide an abrading action more suitable for cutting through the rigid plaster outer cast layer constituting most of the thickness of the cast. Such a blade structure, in some applications is preferred, to the blade structure illustrated in FIG. 6 wherein the arcuate edge portion 40a, 45a of the blade members provides generally identical teeth throughout its extent.

Although the preferred embodiments of this invention have been shown and described, it should be understood that various modifications and rearrangements of the parts may be resorted to without departing from the scope of the invention as disclosed and claimed herein.

What is claimed is:

1. An apparatus for cutting a surgical or orthopedic cast overlying a human or animal body portion comprising:
   a housing;
   motor means mounted to the housing;
   a pair of blade members, each having an arcuate, sawtoothed, edge portion, the edge portions being in juxtaposed relationship, the blades being pivotally mounted relative to the housing for concurrent movement on a common pivot axis;
   transmission means located within the housing and connected between the motor means and the blades, the transmission means having an input connected to the motor and an output connected to the blades, the transmission means, in respnse to energization of the motor means, simultaneously driving the blades for oscillatory movement relative to each other, the juxtaposed edge portions being at least in part simultaneously engageable with the cast to cut the cast and provide a single kerf therein; and a footlike blade guard supported in fixed relationship to the blades, a portion of the guard being positionable between blade portions engageable with the cast and the underlying body portion so as to shield the body portion from contact with the moving blades as the cast is cut, the blade guard having an upper surface engageable with the underside of the cast and a lower surface engageable with the body portion of the human or animal, the sawtoothed edge portions of the blades cooperating with the upper surface of the bladeward to provide a nip area for receiving the underside of the cast engageable with the blade guard upper surface, the sawtoothed, arcuate, edge portions of the blades moving in parallel planes generally perpendicular to the upper surface of the footlike blade guard, the blade guard including an aperture extending between the upper and lower blade guard surfaces, the moving sawtoothed edge portions located at said nip area extending from said upper surface into said aperture to a point between the upper and lower surfaces of the blade guard.

2. An apparatus according to claim 1, wherein at least a portion of dust particles, generated by the cutting of the cast in said nip area, is expelled from said nip area via said aperture provided in the blade guard to preclude clogging of the blades with dust particles.

3. An apparatus for cutting a surgical or orthopedic cast overlying a human or animal body portion comprising:
   a housing;
   an elongated electric motor means mounted to the housing, the elongated motor means being grippable by a user, the housing being located at one end of the motor means, the motor means including a rotatable motor shaft having an end extending into the housing;
   a pair of flat, platelike, blade members, each having an arcuate, sawtoothed, edge portion, the edge portions being in juxtaposed relationship and generally lying along a common curved line, the blades being pivotally mounted relative to the housing for concurrent movement, in parallel planes, on a common pivot axis;
   transmission means located within the housing, the transmission means having a drive shaft connected to the said end of the rotatable motor shaft, the transmission means being connected to the blades, wherein, upon rotation of the drive shaft by the motor shaft, the blades are simultaneously driven in oscillatory movement relative to each other, the blades extending outwardly from the housing wherein the juxtaposed edge portions are at least in part simultaneously engageable with the cast to be cut to provide a single kerf therein; and a footlike blade guard having an elongated leg portion including a first end fixed to the housing and a second distal end spaced from the housing, the blade guard further including a foot portion having a heel end and a toe end, said foot portion also having an upper surface engageable with the underside of the cast and a lower surface engageable with the body portion of the human or animal, the heel end being connected to the said distal end of the leg portion, the toe end of the foot portion extending to the location of said edge portions of the blades, wherein said toe end and a portion of said edge portions interface to provide a nip area for receiving the underside of the cast, the toe end of the foot portion of the blade guard being insertable between the cast and the underlying human or animal body portion to shield the underlying body portion from contact with the moving blades as the cast is cut, the blade guard fast portion including an aperture extending between the upper and lower blade guard surfaces, the moving sawtoothed edge porions located at said nip area extending from said upper surface into said aperture to a point between the upper and lower surfaces of the blade guard.

4. An apparatus according to claim 3 including detent means, and an associated lever member wherein said blade members are removable by release of the detent means actuated by the lever member carried on the housing and actuated by the user.

5. An apparatus according to claim 4 wherein said blade guard is movable to facilitate removal of said blades.

6. An apparatus according to claim 3 wherein said transmission means includes cam members mounted on said drive shaft for simultaneous rotation, said transmission means further including a pair of blade member holders having cam follower portions engageable with said cam members to provide oscillatory movement of said holders relative to each other, said holders being pivotally mounted, on a common pivot axis, to said housing, said holders receiving said blade members.

7. An apparatus according to claim 6 wherein said cam members are constituted by circular bearing means eccentrically mounted on said shaft in opposed relation to each other, said bearings being received by respective apertures in said blade member holders, wall portions of the holders defining the apertures being engageable with the cam members and constituting the said cam follower portions.

8. An apparatus according to claim 3 wherein said blade members are slightly spaced from each other to preclude friction generated heat buildup that could result from the moving blades rubbing together.

9. An apparatus according to claim 3 including means for manually rotating said drive shaft when the motor means is de-energized.

10. An apparatus according to claim 3 wherein said edge portions each include sawteeth projections, the sawteeth projections of one arcuate edge portion extending outwardly away from the other edge portion.

* * * * *

UNITED STATES PATENT AND TRADEMARK OFFICE
CERTIFICATE OF CORRECTION

PATENT NO. : 4,625,405

DATED : December 2, 1986

INVENTOR(S) : H. Dean Hudnutt et al.

It is certified that error appears in the above-identified patent and that said Letters Patent is hereby corrected as shown below:

Column 4, line 55, after "of", insert the following --woven meshlike cloth 14 will ride up onto the top of the--.

Claim 1, line 15, change "respnse" to --response--; and
line 32, change "bladeward" to --bladeguard--.

Claim 3, line 47, change "fast" to --foot--.

Signed and Sealed this

Eighth Day of September, 1987

Attest:

DONALD J. QUIGG

Attesting Officer

Commissioner of Patents and Trademarks